(12) United States Patent
Kim et al.

(10) Patent No.: US 9,999,589 B2
(45) Date of Patent: Jun. 19, 2018

(54) CULTURE MEDIUM OF ADIPOSE-DERIVED STEM CELL, METHOD FOR PREPARING THE SAME, AND COMPOSITION INCLUDING THE SAME FOR PROMOTING HAIR GROWTH

(75) Inventors: Dong Wan Kim, Busan (KR); Mi Jung Seo, Changwon-si (KR); Gwang Lee, Suwon-si (KR); Woo Hong Joo, Changwon-si (KR); Sun Hee Kim, Busan (KR)

(73) Assignee: CHANGWON NATIONAL UNIVERSITY INDUSTRY ACADEMY COOP, Gyeongsangnam (KR)

( * ) Notice: Subject to any disclaimer, the term of this patent is extended or adjusted under 35 U.S.C. 154(b) by 675 days.

(21) Appl. No.: 14/384,044

(22) PCT Filed: Aug. 29, 2012

(86) PCT No.: PCT/KR2012/006907
§ 371 (c)(1),
(2), (4) Date: Oct. 7, 2014

(87) PCT Pub. No.: WO2013/133494
PCT Pub. Date: Sep. 12, 2013

(65) Prior Publication Data
US 2015/0037435 A1 Feb. 5, 2015

(30) Foreign Application Priority Data
Mar. 9, 2012 (KR) .................. 10-2012-0024487

(51) Int. Cl.
| | | |
|---|---|---|
| *A61K 39/12* | (2006.01) |
| *C12N 1/00* | (2006.01) |
| *A61K 8/98* | (2006.01) |
| *C12N 15/85* | (2006.01) |
| *A61K 35/28* | (2015.01) |
| *C12N 5/0775* | (2010.01) |
| *A61Q 7/00* | (2006.01) |
| *C12N 5/077* | (2010.01) |
| *A61K 8/99* | (2017.01) |

(52) U.S. Cl.
CPC .............. *A61K 8/981* (2013.01); *A61K 8/99* (2013.01); *A61K 35/28* (2013.01); *A61Q 7/00* (2013.01); *C12N 5/0653* (2013.01); *C12N 5/0667* (2013.01); *C12N 15/85* (2013.01); *A61K 2800/70* (2013.01); *C12N 2500/84* (2013.01); *C12N 2506/1384* (2013.01); *C12N 2510/00* (2013.01)

(58) Field of Classification Search
None
See application file for complete search history.

(56) References Cited

U.S. PATENT DOCUMENTS

| | | | | |
|---|---|---|---|---|
| 7,531,355 | B2* | 5/2009 | Rodriguez | C12N 5/0667 435/325 |
| 2004/0166096 | A1* | 8/2004 | Kolkin | C12N 5/0653 424/93.7 |
| 2005/0260748 | A1* | 11/2005 | Chang | C12N 5/0672 435/366 |
| 2007/0160644 | A1* | 7/2007 | Kenan | A61L 27/34 424/423 |
| 2007/0275362 | A1* | 11/2007 | Edinger | C12N 5/0605 435/1.2 |
| 2008/0219957 | A1* | 9/2008 | Lim | C12N 5/0662 424/93.7 |
| 2009/0053182 | A1* | 2/2009 | Ichim | A61K 35/545 424/93.7 |
| 2009/0304654 | A1* | 12/2009 | Lue | C12N 5/0667 424/93.21 |
| 2010/0015104 | A1* | 1/2010 | Fraser | C12N 5/0653 424/93.7 |

(Continued)

FOREIGN PATENT DOCUMENTS

| | | |
|---|---|---|
| EP | 1303589 B1 | 9/2007 |
| KR | 10-2010-0097574 A | 9/2010 |

(Continued)

OTHER PUBLICATIONS

Park et al. Biomedical Research 31 (1) 27-34, 2010.*
Seo, Mi-Jeong, "Hair growth promoting effect of culture medium of primary and immortalized Adipose-Derived Stem Cells", Chang Won University Graduate School, Biology, Thesis for Master's Degree (2011).

*Primary Examiner* — Chris R Tate
*Assistant Examiner* — Douglas F White
(74) *Attorney, Agent, or Firm* — Renner Kenner Greive Bobak Taylor & Weber

(57) ABSTRACT

Provided are a culture medium of an adipose-derived stem cell, a method for preparing the same, and a composition for promoting hair growth, in which the composition includes the culture medium. The adipose-derived stem cell (ADSC-T) according to the present invention exhibits long lifespan, improved cell proliferation rate, and extended proliferation period, as compared with a primary adipose-derived stem cell (ADSC), and thus, the adipose-derived stem cell (ADSC-T) can be usefully used for the study about the adipose-derived stem cell and the mass production of the culture medium of the adipose-derived stem cell. In addition, according to the present invention, the culture medium of the adipose-derived stem cell (ADSC-T) that expresses a T antigen of SV40 exhibits excellent hair growth effectiveness and can be usefully used as a raw material for the hair loss prevention and hair growing agents.

2 Claims, 8 Drawing Sheets

(56) References Cited

U.S. PATENT DOCUMENTS

2010/0304477 A1* 12/2010 Buscher ............... C12N 5/0667
                                                435/325
2011/0268708 A1* 11/2011 Lin ..................... A61K 9/0019
                                                424/93.7
2011/0318830 A1* 12/2011 Briggs ............... C07K 14/4702
                                                435/350

FOREIGN PATENT DOCUMENTS

KR          10-1061464 B1    9/2011
WO     WO 2010056808 A2 *    5/2010    ......... C07K 14/4702

* cited by examiner

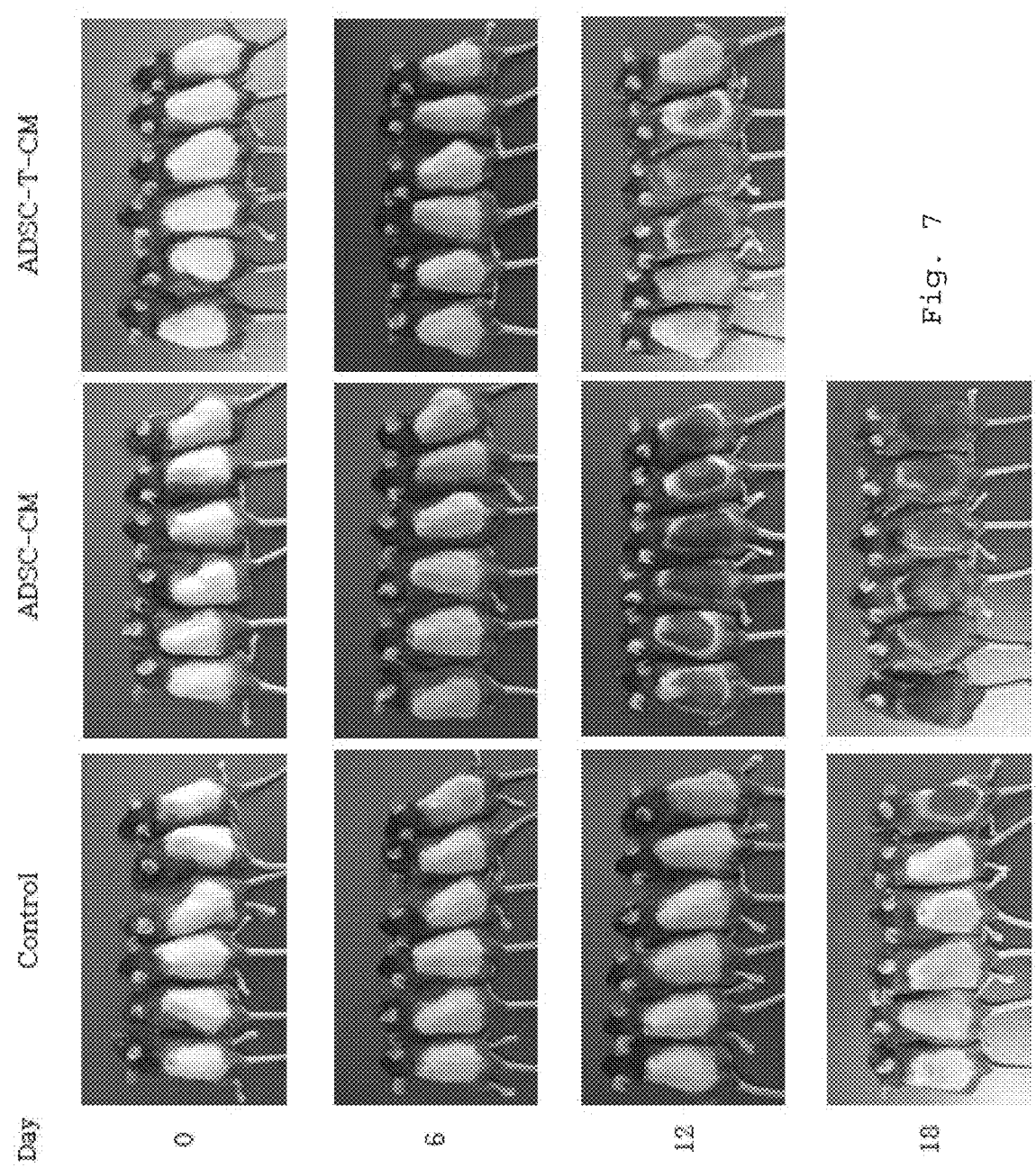

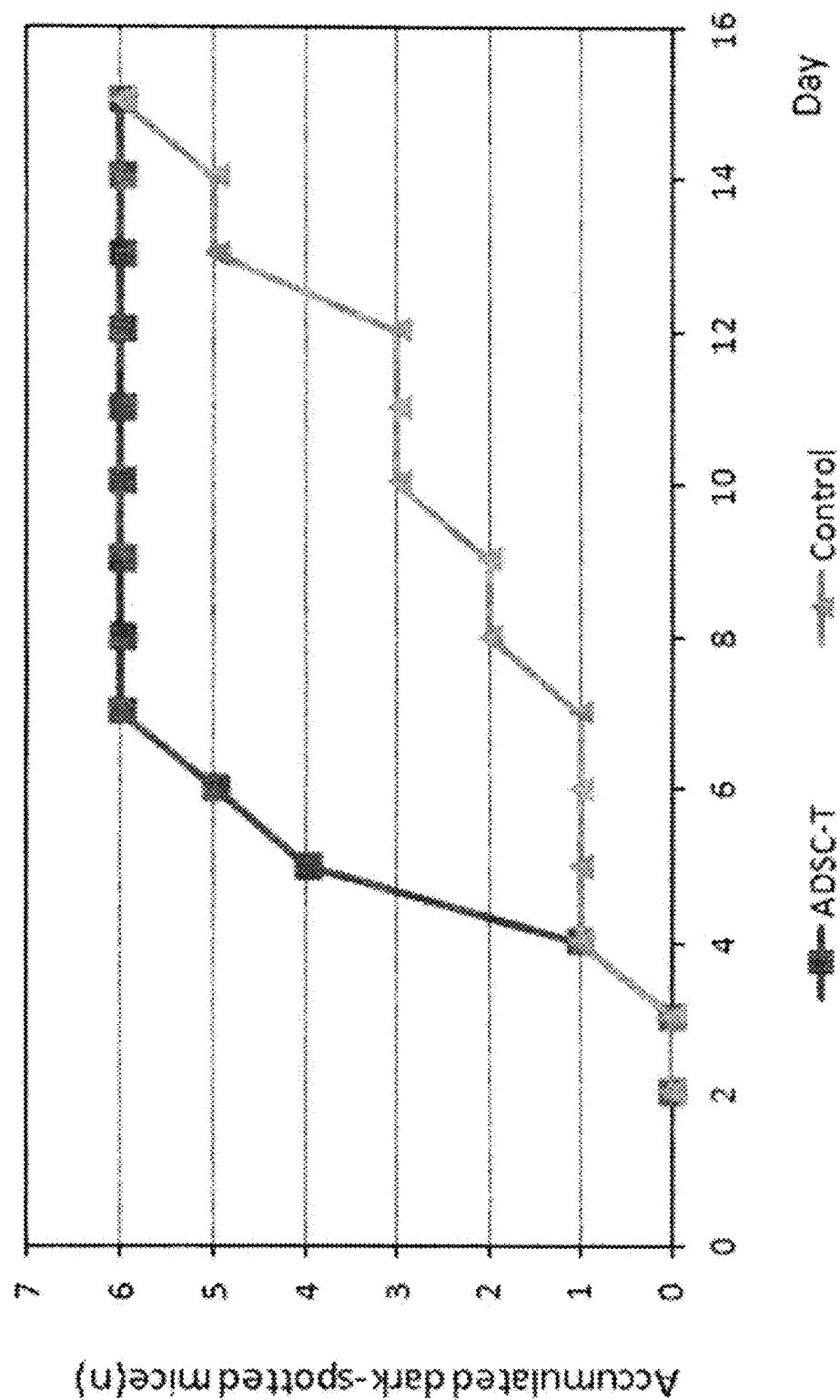

CULTURE MEDIUM OF ADIPOSE-DERIVED STEM CELL, METHOD FOR PREPARING THE SAME, AND COMPOSITION INCLUDING THE SAME FOR PROMOTING HAIR GROWTH

TECHNICAL FIELD

The present invention relates to a culture medium of an adipose-derived stem cell, a method of preparing the culture medium, and a composition for promoting hair growth, in which the composition includes the culture medium.

BACKGROUND ART

As the interest on beauty treatment is increased, there is also a rising interest on treating hair loss.

Hairs do not have a physiologic function that is directly important for life, but have the functions, including the mitigation of external shock, an anti-ultraviolet function, the human body protection from external stimulus, and the absorption of heavy metals such as arsenic, mercury, and zinc, which are unnecessary for the human body to eliminate them from the body. The cycle of hairs is divided into the growing period (anagen) that grows hairs, the degeneration period (catagen) that slows the metabolic process down while stopping the growth and reducing a hair bulb, and the suspension period for (telogen) that reduces a hair follicle and rides a hair root up to fall hairs out. The hairs have the hair cycle, in which because new hairs are generated on the same spots, the old hairs have fallen and then the growing period has come, and thus, the growth and the loss of the hairs are repeated in one's lifetime. The hair loss is the state where the hairs are not present on the normal spots that should have the hairs. The causes thereof are as follows: a decline in the function of trichocyst due to the participation of male hormone, a decline in the scalp physiological function, the focal hemodynamic dysfunction due to the scalp tension, innutrition, stress, the side effect by drugs, a genetic factor, chemicals, and diseases such as leukemia, tuberculosis, and malignant lymphoma. In addition to the above functions, the treatment of hair loss is very important from the viewpoint of the quality of life, since when the hair loss is severe, there may be some problems in the social life and the psychological shrinking, and thus, it can seriously affect the social life.

As a hair loss-treating method that is currently used the most, a follicular unit hair transplantation for transplanting one's own hairs, and a medicine treatment using minoxidil and propecia are widely used. In the case of using minoxidil, the nutrition supply to hair cells through vasodioatation is increased and the hair growth is induced by a potassium channel opening effect. In the case of using propecia, the hair growth is induced by the effect on inhibiting the generation of dihydrotestosterone (DHT). However, as for the above two medicines, the effectiveness of hair growth is exhibited at the time of treating, but when the treatment is stopped, the hair loss is again exhibited. Therefore, the medicines have a greater hair loss prevention effect than a hair growth effect. In the case of using propecia, there may be side effects such as sexual dysfunction and the delivery of deformed child.

Recently, a gene therapy has been developed, in which genes related to hair loss are delivered to a hair follicle or the gene expression is blocked. However, the safety and the effectiveness of treatment are unclear and the treatment cost is high, so that the clinical application thereof is not easy.

For this reason, a hair loss treating method using a stem cell has the limelight other than the gene treatment.

It has been confirmed that a stem cell can be self-replicated in a un-differentiation state and can be subjected to the multilineage differentiation into the cells of the other tissues, and is present in the many tissues. First of all, a marrow derived stem cell derived from the marrow is known. Since then, it has been known that an adult stem cell is present on anywhere of our body, for example, peripheral blood, placenta, skin, nervous tissue, fat, muscles, and the like, as well as umbilical cord and blood. Meanwhile, the adipose-derived stem cells are a cell derived from a mesenchymal tissue, like a marrow derived stem cell, can be differentiated into various types of cells, such as an adipocyte, a fibroblast, a smooth muscle cell, an endotheliocyte, and a preadipocyte cell, and also can be differentiated into the epithelium, cartilage, nerve, fat, muscles cells, and the like. In addition, an adipose-derived stem cell is easily taken since an adipose tissue that is a material therefor can be additionally mass-extracted during suction lipectomy, and can be easily isolated by enzyme, and after transplanting the adipose-derived stem cell, the reduced disease incidence was reported.

However, currently, as a hair loss treating method using a stem cell, a method for inducing the differentiation into follicular cells by directly injecting the stem cells to the region exhibiting the hair loss or hairless is mainly used. However, such a method has problems in that if the stem cells are not autologous stem cells, the treatment is impossible, the treatment effect is not continuously maintained, and it takes for a long period of time and high costs. In order to improve the above problems, the attempt for treating hair loss, using a culture medium produced at the time of culturing the stem cells, not using the stem cells, is being made.

Meanwhile, the transduction signaling molecules that affect hair growth are an external factor and an internal factor. The external factor may be a growth factor and cytokine. The stem cells secrete a growth factor and a protein active substance, and thus, the culture medium that cultures the stem cells includes the above substances. In order to use the culture medium as a hair growing agent, the culture medium should be produced in bulk. However, in the case of using an adipose-derived stem cell, at the time of culturing the adipose-derived stem cells for a long period of time in vitro, the adipose-derived stem cell exhibits a replicative senescence, in which a cell proliferation ability is gradually decreased by a cellular senescence, and finally, the growth is stopped, and also exhibits reduced differentiation ability. Therefore, in order to overcome the above-described problems, the need of the technique capable of producing a large amount of the culture medium is urgently needed by increasing the lifespan of the cells and the growth speed of the cells while the characteristics of the adipose-derived stem cell are maintained.

DISCLOSURE

Technical Problem

The present inventors confirmed that the lifespan of the adipose-derived stem cell introduced with an T antigen of SV40, was increased and exhibited high proliferation rate, and also the culture medium of the adipose-derived stem cell had an excellent hair growth effectiveness, during the study on the method for increasing the lifespan of the cells and improving the proliferation rate while maintaining the characteristics of the adipose-derived stem cell. Therefore, the present inventors completed the present invention.

Therefore, an object of the present invention is to provide a culture medium for an adipose-derived stem cell, a method for preparing the culture medium, and a composition for promoting hair growth, in which the composition includes the culture medium prepared by the above-described method.

Technical Solution

An exemplary embodiment of the present invention provides a culture medium for an adipose-derived stem cell and a method for preparing the culture medium.

Another exemplary embodiment of the present invention provides a composition for promoting hair growth, in which the composition includes the culture medium for an adipose-derived stem cell.

Advantageous Effects

The adipose-derived stem cell (ADSC-T) according to the present invention exhibits long lifespan, improved cell proliferation rate, and extended proliferation period, as compared with a primary adipose-derived stem cell (ADSC), and thus, the adipose-derived stem cell (ADSC-T) can be usefully used for the study about the adipose-derived stem cell and the mass production of the culture medium of the adipose-derived stem cell. In addition, according to the present invention, the culture medium of the adipose-derived stem cell (ADSC-T) that expresses a T antigen of SV40 exhibits excellent hair growth effectiveness and can be usefully used as a raw material for the hair loss prevention and hair growing agents.

DESCRIPTION OF DRAWINGS

FIG. 7 is a diagram illustrating the abdominal regions of hair loss mouse model observed with the naked eye, in which normal saline solution was applied on the abdominal region as a control group, and the culture medium of ADSC-T was applied on other abdominal region.

FIG. 8 is a diagram illustrating the days that are needed for exhibiting blue spots after applying the abdominal regions without the hairs with normal saline solution or the culture medium of ADSC-T, after removing the hairs of the abdominal regions of the hair loss mouse models (6 mice).

BEST MODE

Figure 1:
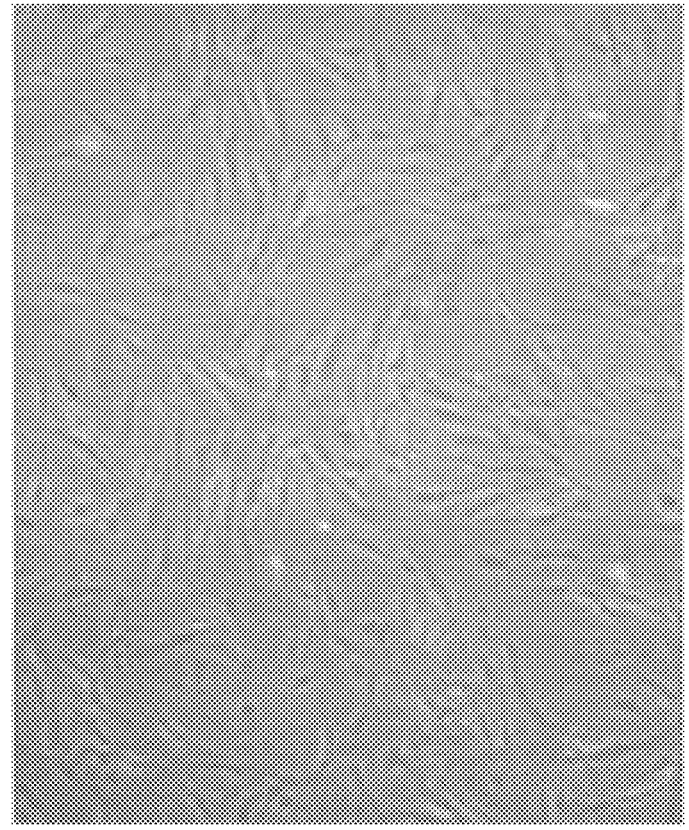
FIG. 1A is a diagram illustrating all the cells isolated from suctioned adipose tissues, which were observed with a microscope after spreading all the cells isolated from suctioned adipose tissues on a plate.
FIG. 1B is a diagram illustrating the cells, which were observed with a microscope after sub-culturing only the cells attached on the plate after removing the floating cells (×100 magnification, respectively).
Figure 1:

Hereinafter, the present invention will be described in more detail.

The present inventors expected that on the basis that the lifespan of various cells were extended by the expression of a T antigen of SV40, the lifespan of the adipose-derived stem cell could be extended by isolating stem cells from suctioned adipose (Adipose-derived stem cells, ADSC), and then introducing the vector expressing a T antigen of SV40 in order to increase the proliferation rate of the isolated adipose-derived stem cells and extend the proliferation lifespan.

In order to identify the above content, pEF321β-T plasmid that is a vector expressing a T antigen of SV40 is introduced into an adipose-derived stem cell. As a result, it can be confirmed that the lifespan of the adipose-derived stem cell expressing a T antigen of SV40 is extended and the proliferation rate thereof is improved.

From the above-described result, it can be confirmed that when the adipose-derived stem cell expressing a T antigen of SV40 is used, the culture medium of the adipose-derived stem cell can be produced in bulk, and thus, a raw material of a composition for promoting hair growth, in which the raw material includes the culture medium of the adipose-derived stem cell as an effective component, can be obtained in bulk.

Such an adipose tissue has an advantage in that the adipose tissue can be extracted in bulk. It is reported that an adipose-derived stem cell contained in the above tissue can be differentiated into an epithelial cell, a cartilage cell, an osteogenic cell, an adipocyte, a nerve cell, a cartilage cell, a muscular cell, and the like. In the recent studies, it is found that the adipose-derived stem cell has an ability for promoting the muscle regeneration ability and neurovascular differentiation (Zuk et al., Tissue Eng., 7:211, 2001; Rodriguez et al., BBRC., 315:255, 2004; Brzoska et al., BBRC, 330:142, 2005; Safford et al., BBRC, 294:371, 2005; Biomaterials, 25:3211, 2004; Fujimura et al., BBRC, 333:116, 2005; U.S. Pat. No. 6,777,231).

In the present invention, the liposuction is one of the beauty treatment or plastic operations for removing adipose, and means the operations that pull out adipose with a vacuum pump or using the pressure of syringe after making an incision of the adipose part.

In the present invention, "SV40 (Simian Virus 40)" is a virus that belongs to a polyoma virus family, a polyoma virus genus, and simian virus 40 species, has a circular double-strand dielectric formed of 5245 bases, has a wide host range, and thus, is used as a transformation vector of a cell.

The "T antigen" of SV40 is an early protein that is synthesized at the beginning of the infection of SV40 that is a virus leading to a tumor, and is a protein contributing to the canceration of the infected cell. The T antigen has a function of suppressing the activity of a tumor inhibitory gene product (p53, and the like) by binding with the tumor inhibitory gene product (p53, and the like) of the cell during the transformation of the cells, and thus, is applied to the immortalization of various cells.

In order to achieve the object of the present invention, the present invention provides a method for preparing a culture medium of an adipose-derived stem cell (ADSC-T), in which the method includes (a) culturing the adipose-derived stem cell after isolating the adipose-derived stem cell through a centrifuge after treating an enzyme, collagenase thereto; (b) preparing an adipose-derived stem cell (ADSC-T) expressing a T antigen of SV40 by transfecting a plasmid expression vector (pEF321β-T) into the adipose-derived stem cell cultured from the above step (a); and (c) obtaining a culture medium by culturing the adipose-derived stem cell (ADSC-T) prepared as described above.

The method for preparing a culture medium of an adipose-derived stem cell according to the present invention will be described in detail in sequence as follows:

The above step (a) is a step culturing an adipose-derived stem cell isolated from a suctioned adipose tissue, in which first, an enzyme, collagenase, is mixed with the suctioned adipose tissue in a weight ratio of 1:1, treated at 30 to 40° C. for 40 to 50 minutes, and then centrifuged to isolate the adipose-derived stem cell.

The above enzyme "collagenase" is an enzyme promoting the hydrolysis of collagen, and plays a role in isolating each of the adipose stem cells by decomposing the collagen of an adipose tissue.

The centrifugation may be carried out at 500 to 1000 G for 2 to 5 minutes, and preferably, at 800 G for 3 minutes to obtain the supernatant. After the lipid and adipocyte layer that are floated on the supernatant are removed, cellular residue is removed using a filter. The filter is preferably a 100 μm filter, but it is not limited thereto.

After removing the cellular residue, normal saline solution is added thereto, and then the centrifugation is repeated to clean. The centrifugation may be carried out at 150 to 500 G for 2 to 5 minutes, and preferably, may be carried out at 300 G for 3 minutes.

The isolated adipose-derived stem cell (ADSC) is cultured in Dulbecco's Modified Eagle Media (DMEM) added with 10% Fetal Bovine Serum (FBS), 100 units/ml of penicillin, and 100 μg/ml of streptomycin in an incubator of 37° C. and 5% $CO_2$. When the confluence of the cells reaches 80 to 90%, the sub-culture is carried out. As the above culture method, the cell culture method that is known in the art may be applied.

The above step (b) is a step for preparing an adipose-derived stem cell (ADSC-T) expressing a T antigen of SV40, in which a plasmid expression vector (pEF321β-T) is transfected into the adipose-derived stem cell isolated in the above step (a) to obtain the adipose-derived stem cell (ADSC-T) expressing a T antigen of SV40.

The "vector" is DNA capable for a desired DNA fragment to be introduced into a host cell for a DNA recombination experiment, and the vector DNA is cleaved and opened by restriction enzymes, and then connected by inserting a desired DNA fragment, thereby introducing the desired DNA fragment into a host cell. The vector DNA connecting the desired DNA fragment is inserted into chromosome DNA, and thus, distributed to each of the cells according to the host cell division. Therefore, the desired DNA fragment is maintained, and thus, is connected from generation to generation.

The plasmid expression vector, "pEF321β-T" means the plasmid including nucleic acid sequences encoding a T antigen of SV40.

The "transfection" is a means to cause a DNA introduction and infection by injecting gene DNA, plasmid DNA, virus DNA.RNA, and the like through the culture medium of cells or suspension of cells into a cell. In detail, the transfection of the expression vector may be carried out by using all of the available transfection methods including a calcium phosphate transfection, an electroporation, a microinjection, a liposome injection, and the like, which are known in the art. In addition, DNA can be introduced into eukaryotic cells using virus or bacteria as a carrier.

For example, a method of introducing the pEF321β-T plasmid using the electroporation may be carried out by using a method including mixing an adipose-derived stem cell with a plasmid in a nonserum culture medium, preferably, a nonserum DMEM, and then performing an electric shock, but the present invention is not limited thereto. In addition, the plasmid can be introduced by using the electroporation protocol that is known in the art.

For the cell introduced with a foreign gene, the expression of the gene introduced by the culture for a certain time is induced, and then whether or not the expression thereof is induced should be verified. The culture for expressing the introduced gene is preferably carried out at 5% CO incubator at 37° C., but the present invention is not limited thereto. The gene introduced for the present invention is a gene expressing a T antigen of SV40, and whether or not the expression of T antigen is carried out can be verified by detecting the T antigen expressed in an adipose-derived stem cell through an antigen-antibody binding reaction using an antigen that is specifically bound to the T antigen. In detail, it can be verified by using a general enzyme immunoassay (ELISA), a radioimmunoassay (RIA), a sandwich assay, an immunochitochemical staining, an antigen-antigen aggregation assay, and the like. In one embodiment of the present invention, whether or not the expression of T antigen is carried out is verified with a western blot assay and fluorescent antibody staining assay.

The above step (c) is a step for obtaining a culture medium by culturing an adipose-derived stem cell (ADSC-T), in which the culture medium is obtained by culturing ADSC-T cells in $1 \times 10^5$ cell/ml; sub-culturing the cells after the cell confluence reaches 80%; and collecting the culture medium at 2 days after the cell confluence reaches 70 to 90%.

The above-obtained culture medium is centrifuged to remove cell residue and collect only a supernatant. The centrifugation is carried out at 500 to 1000 G for 2 to 5 minutes, and preferably, at 800 G for 3 minutes.

The culture medium of an adipose-derived stem cell (ADSC-T) according to the present invention, which is prepared by using the above-described method, has excellent effect on hair proliferation in a hair loss mouse model. Therefore, the culture medium of an adipose-derived stem cell according to the present invention may be usefully used as a raw material for a hair growth accelerator.

In addition, the present invention provides a composition for promoting hair growth, in which the composition includes a culture medium of an adipose-derived stem cell (ADSC-T) expressing a T antigen of SV40 as an effective component.

The composition according to the present invention includes a pharmaceutical composition and/or cosmetic composition.

For the pharmaceutical composition, the composition may include a pharmaceutically acceptable carrier, and may be formulated in a formulation for dermal administration, for example, a liquid medicine, suspension, emulsion, lotion medicine, ointment medicine, and the like. The pharmaceutically acceptable carrier includes aqueous diluents or solvent such as phosphate buffered saline, purified water, and sterile water, or non-aqueous diluents or solvent such as propylene glycol, and olive oil. In addition, if necessary, it may include a wetting agent, a flavoring agent, a preserving agent, and the like. The culture medium of an adipose-derived stem cell, which is included in the pharmaceutical composition, may be properly selected according to the condition and weight of a patient, the degree of disease, a drug type, and an administration route and period. For example, the culture medium of an adipose-derived stem cell may be administrated in an amount of 0.01 to 100 mg/kg per a day, and preferably 0.1 to 10 mg/kg per a day. The administration may be carried out once a day or several times a day.

The cosmetic composition may be prepared in various types according to a general cosmetic preparing method using the culture medium of an adipose-derived stem cell. For example, the cosmetic composition may be prepared in a type, such as an enterotropic product, shampoo, hair lotion, hair cream, and hair gel, and may be used by diluting it with cleansing solution, astringency solution, and moisturizing solution. In addition, the cosmetic composition may include general adjuvants such as stabilizer, a dissolving agent, vitamins, pigments, and a flavoring agent, which are generally used in the cosmetic composition field. For the cosmetic composition, the content of the culture medium may be included in an effective amount for achieving an effect on promoting hair growth, for example, 0.001 to 10 wt %, and preferably about 0.01 to 1 wt % with respect to the total weight of the composition.

EXAMPLES

Hereinafter, preferred Examples will be described to enhance content understanding of the present invention. However, the following Examples are provided only for the more easy understanding of the present invention, but the present invention is not limited to the following Examples.

<Example 1> Isolation of Adipose-Derived Stem Cell from Adipose Tissue and Cultivation of Adipose-Derived Stem Cell 1. Isolation of Stem Cell from Adipose Tissue The isolation of an adipose-derived stem cell (ADSC) was extracted from an adipose tissue collected from a patient who undergoes a liposuction with patient consent. In detail, the isolated adipose tissue was washed with phosphate buffered saline (PBS), mixed with 0.075% collagenase (Sigma) in a weight ratio of 1:1, and then reacted at 37° C. for 45 minutes. After treating the enzyme, the adipose tissue thus obtained was centrifuged at 800 G for 5 minutes to obtain a supernatant. The lipid and adipocyte layer that were floated on the supernatant were removed, and then filtered through a 100 μm filter to remove cellular residue. Normal saline solution was added to the filtrate thus obtained, and the filtrate thus obtained was centrifuged at 300 G for 3 minutes to wash the cells about 2 to 3 times. As a result, an adipose-derived stem cell (ADSC) was obtained.

2. Cultivation of Adipose-Derived Stem Cell (ADSC)

The adipose-derived stem cell (ADSC) obtained from the above (1) was cultured in Dulbecco's Modified Eagle Media (DMEM) including 10% fetal bovine serum (FBS), 100 units/ml penicillin, and 100 μg/ml streptomycin in a 37° C. and 5% $CO_2$ incubator. The isolated adipose-derived stem cell (ADSC) included red blood cells, and in order to remove the red blood cells, buffer solution for dissolving the red blood cells might be used, but when the buffer solution for dissolving the red blood cells was used, the number of the adipose-derived stem cells (ADSC) was apt to decrease. Therefore, at the beginning of the cultivation, the isolated adipose-derived stem cells (ADSC) in an original state were cultured with red blood cells. For this reason, at the beginning of the cultivation, the adipose-derived stem cells (ADSC) were cultured in a state of mixing them with the red blood cells (FIG. 1A). After one day of initial cultivation, it was considered that the adipose-derived stem cells (ADSC) were completely attached on a plate, and then, the cells were washed with PBS twice to remove floated cells and red blood cells. The red blood cells which were not completely removed were removed by trypsinization during sub-cultivation. When the cell confluence reached to 80 to 90% of the incubator, the sub-cultivation was carried out.

After 2 to 3 days of initial cultivation, it was confirmed that the adipose-derived stem cells (ADSC) having fibroblast morphology were exhibited. Since then, after sub-culturing the cells into a 10 cm plate, the shape of the adipose-derived stem cell (ADSC) was observed. As a result, it was confirmed that the adipose-derived stem cells (ADSC) exhibited in the same shape as fibroblast like other adult stem cells (FIG. 1B).

<Example 2> Confirmation of Differentiation Ability of Adipose-Derived Stem Cell (ADSC) into Adipocyte In order to confirm the adipose-derived stem cells (ADSC) isolated in Example 1 into an adipocyte, the differentiation of the adipose-derived stem cell (ADSC) into an adipocyte was induced using the medium for inducing an adipocyte differentiation for 4 weeks, and then, whether or not the differentiation thereof into an adipocyte was carried out was confirmed.

As the medium for inducing an adipocyte differentiation, Preadipocyte Differentiation Medium available from PromoCell was used, and as a medium for maintaining the adipocyte differentiated, Adipocyte Nutrition Medium available from PromoCell was used.

In detail, the differentiation of the adipose-derived stem cells (ADSC) was induced by culturing the cells in the medium for inducing the adipocyte differentiation for 10 days while exchanging the medium at 3 days intervals. Since then, the medium was changed with the medium for maintaining the adipocyte, and then the cells were further cultured for 20 days. The cultured cells were fixed in 10% formalin, and stained with 60% Oil-Red O solution to visualize lipid droplet in a cell.

Figure 2:
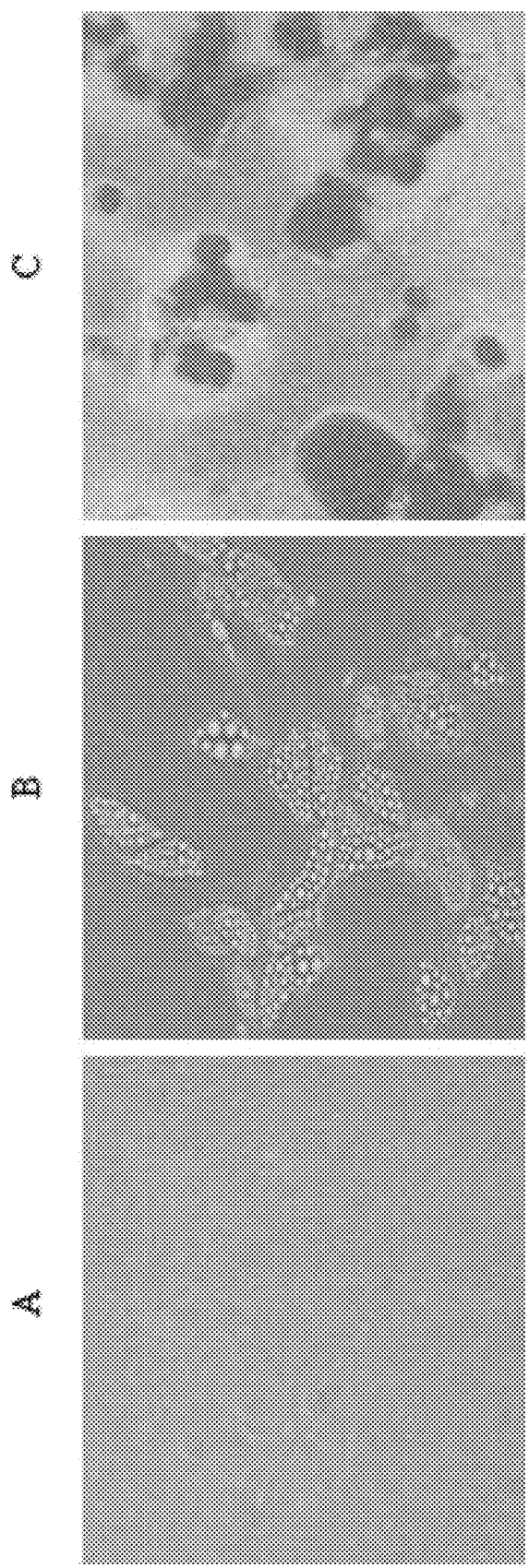
FIG. 2 is a diagram illustrating the result illustrates the result of staining the cells with Oil-Red O, for confirming whether or not the adipose-derived stem cell (ADSC) was differentiated into an adipocyte [(A) before differentiation-inducing the adipose-derived stem cell, (B) after 30 days of the differentiation-induction, and (C) the results of staining the cells with Oil-Red O after 30 days of the differentiation-induction].

The results are shown in FIG. 2 [(A) before differentiation-inducing the adipose-derived stem cell, (B) after 30 days of the differentiation-induction, and (C) the results of staining the cells with Oil-Red O after 30 days of the differentiation-induction].

As illustrated in FIG. 2, it was confirmed by observing the lipid droplet that was a specific adipocyte in the adipose-derived stem cell (ADSC) after 30 days of the cultivation that the cells were differentiated into an adipocyte. In addition, after 30 days of the cultivation, as a result of staining the cells with Oil-Red O, it was confirmed by observing the lipid droplet that was redly stained, the cells were differentiated into an adipocyte (C), and also it was confirmed that the cells that were not stained were not differentiated into an adipocyte (A). Therefore, it was confirmed that the adiposite-derived stem cells (ADSC) have ability capable of being differentiated into a normal adipocyte.

<Example 3> Establishment of ADSC-T Cell Line by Expression of T Antigen of SV40 and Characteristics of ADSC-T 1. Transfection In order to stably express a T antigen of SV40 in adipose-derived stem cells (ADSC), pEF321β-T plasmid DNA was introduced into the adipose-derived stem cells (ADSC) using an electroporation. In detail, the plasmid vector, pEF321β-T and 1×10 adipose-derived stem cells were mixed in 800 µl of serum-free DMEM, and added into a 0.4 cm$^2$ cuvette. Then, an electric shock was applied thereto. The electric shock was carried out at 160 V and 15 msec using Gene Pluser X cell Electroporation System (BIO-RAD).

The adipose-derived stem cells that form high density focus by introducing the plasmid vector, pEF321β-T into the cells were subjected to typsinization after covering a penicillin cap, and then the cells were cloned. Then, culturing the cells in a 24 well plate, and then sub-cultured when the cells reaches 80 to 90% of the incubator. The cell line thus obtained was called ADSC-T.

Figure 3:
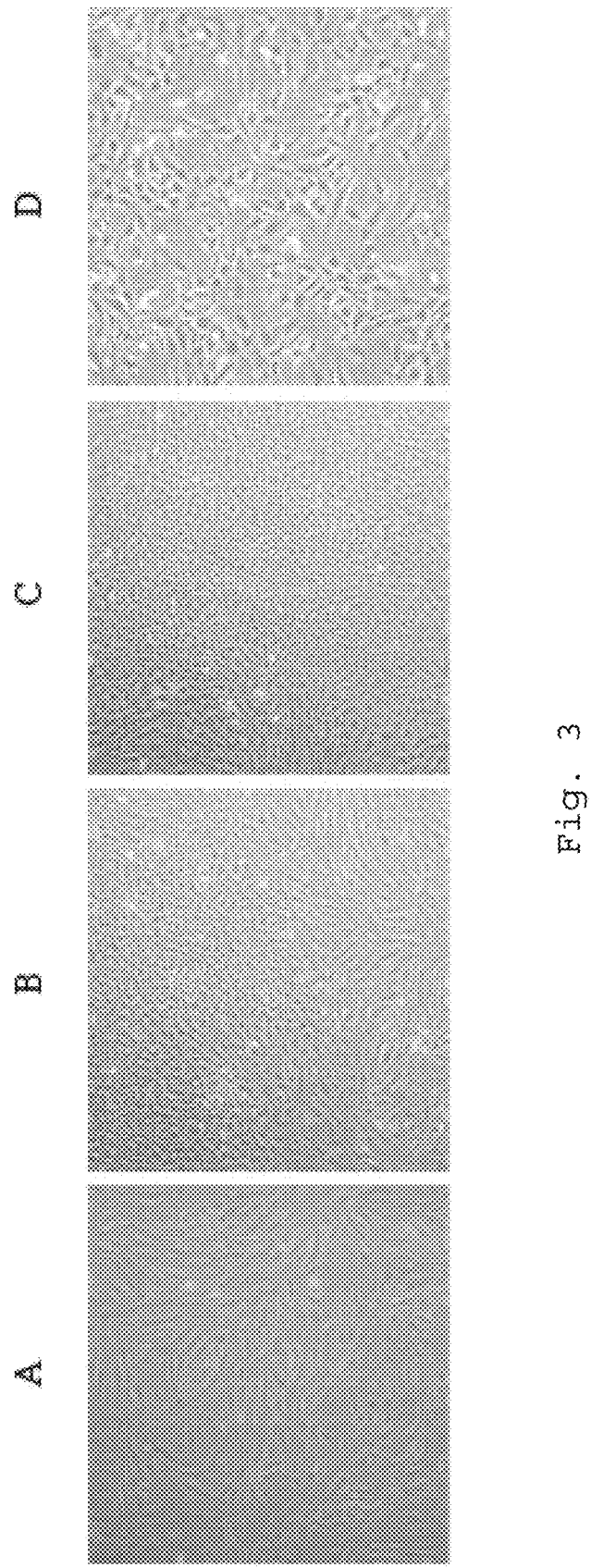
FIG. 3 is a diagram illustrating the morphological changes of the ADSC-T cells, in which the changes were observed with a microscope [(A) an adipose-derived stem cell (primary ADSC), (B, C) a high-density cell group (high-density focus) of the adipose-derived stem cell formed by introducing pEF321 β-T plasmid, and (D) the ADSC-T cells produced by culturing the cells obtained the high-density cell group] (×100 magnification, respectively).

The morphological change of ADSC-T cell is shown in FIG. 3.

As illustrated in FIG. 3A, it was confirmed that in the case of primary adipose-derived stem cells (ADSC), monolayer was formed by stopping the cell proliferation due to contact inhibition in a type of fibroblast having long and large size of the cell. In addition, as illustrated in FIGS. 3B and 3C, it was confirmed that the adipose-derived stem cells (ADSC-T) which had expressed T antigen of SV40 by introducing pEF3211β-T plasmid into the primary adipose-derived stem cells were not affected with the contact inhibition, and the cells were overlapped and grown on the monolayer, thereby forming high-density focus. In addition, as illustrated in FIG. 3D, it was confirmed that the cell size of the ADSC-T was small, and thus, the cells were changed in a type of spindle shape. It can be estimated that the cell morphological change of the ADSC-T occurs due to the expression of a T antigen of SV40.

2. Fluorescent Antibody Staining Method—Whether or not T Antigen of ADSC-T Cell is Expressed.

In order to confirm the expression of a T antigen in ADSC-T cells, the fluorescent antibody staining method was carried out using a monoclonal antibody to a T antigen of SV40 and an anti-mouse IgG marked with fluorescein isothiocyanate (FITC), and then the T antigen was observed under UV. At this time, a COS-1 cell was used as a control group, and the COS-1 cell was prepared by using a T antigen of SV40, and in the case of using the COS-1 cell, whether or not the T antigen of SV40 of the ADSC-T cells was expressed could be compared.

In detail, the ADSC-T cells and COS-1 cells were fixed for 18 minutes with the solution mixed with 1:1 of ethanol and acetone. The fixed cells were washed with PBS, and then cultured along with a monoclonal antibody of a mouse, which is specifically bound, at 37° C. for 1 hour. The cultured cells were washed with PBS, and then cultured along with an anti-mouse of rabbit, marked with FITC, at 37° C. for 1 hour. The cultured cells were observed through a fluorescence microscope.

Figure 4:
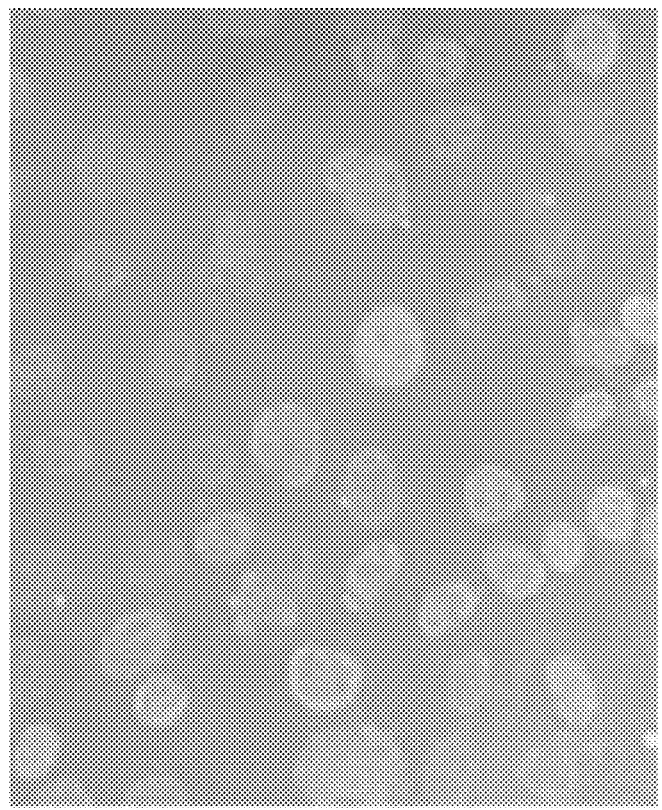
FIG. 4 is a diagram illustrating a SV40 T antigen expressed in the ADSC-T and the COS-1 cells used as a control group, in which the SV40 T antigen was observed by a fluorescent antibody staining method.
Figure 4:
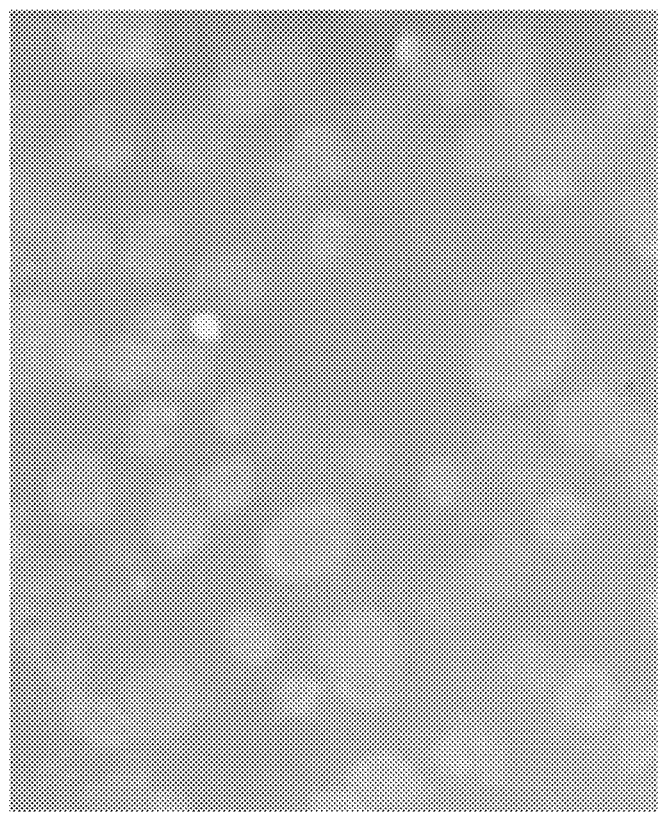

The results are illustrated in FIG. 4.

As illustrated in FIG. 4, it was confirmed that the ADSC-T cells isolated from high-density focus were stained with the monoclonal antibody to a T antigen of SV40, and T antigen was expressed like the COS-1 cells.

3. Western Blotting Assay—Whether or not T Antigen of ADSC-T Cells is Expressed

The total cell extract from each of three ADSC-T cells was prepared, and then a T antigen of SV40 present in the cells was detected by using a western blotting. In detail, the extract of each of the cells including the same amount of the protein was subjected into an electrophoresis on a 10% SDS-polyacrylamide gel, and then transferred into a nitro cellulose membrane. After binding with the monoclonal antibody (IgG) of the mouse that was specifically bound to the T antigen of SV40, and then the nitro cellulose membrane was colored with an anti-mouse IgG bound with peroxidase.

Figure 5:
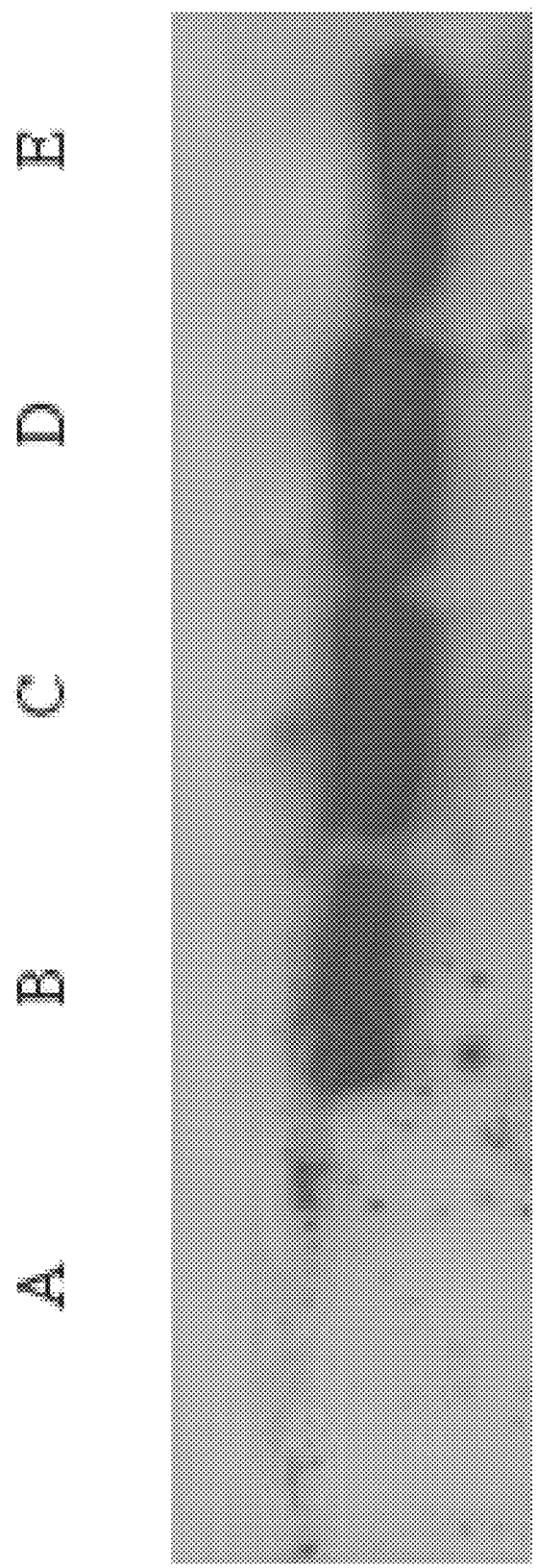
FIG. 5 is a diagram illustrating the result of a western blotting analysis of a T antigen of the ADSC-T cell using an monoclonal antibody of a T antigen [(A) a primary adipose-derived stem cell, (B, C, D) ADSC-T, and (E) COS-1].

The results are illustrated in FIG. 5.

As illustrated in FIG. 5, it was confirmed from the results of the western blotting that the T antigen was expressed in three ADSC-T cells (B, C, and D) like the COS-(E) as a positive control group, and the T antigen was not expressed in the primary adipose-derived stem cell (primary ADSC) that was a negative control group (A).

From the above results, it was confirmed that the T antigen was stably expressed in the ADSC-T cell line isolated, the cell proliferation was increased by the T antigen, and the cell shape was changed.

<Example 4> Proliferation Rate of ADSC-T Cell Established by T Antigen of SV40

The cell proliferation rates of the ADSC-T established by a T antigen of SV40 and a primary adipose-derived stem cell (primary ADSC) were measured and then compared. When the cell confluence reached 80% at the time of culturing the cells, the sub-cultivation was carried out and the cells were counted every sub-cultivation times, and the cell growth curve was prepared and then compared.

Figure 6:
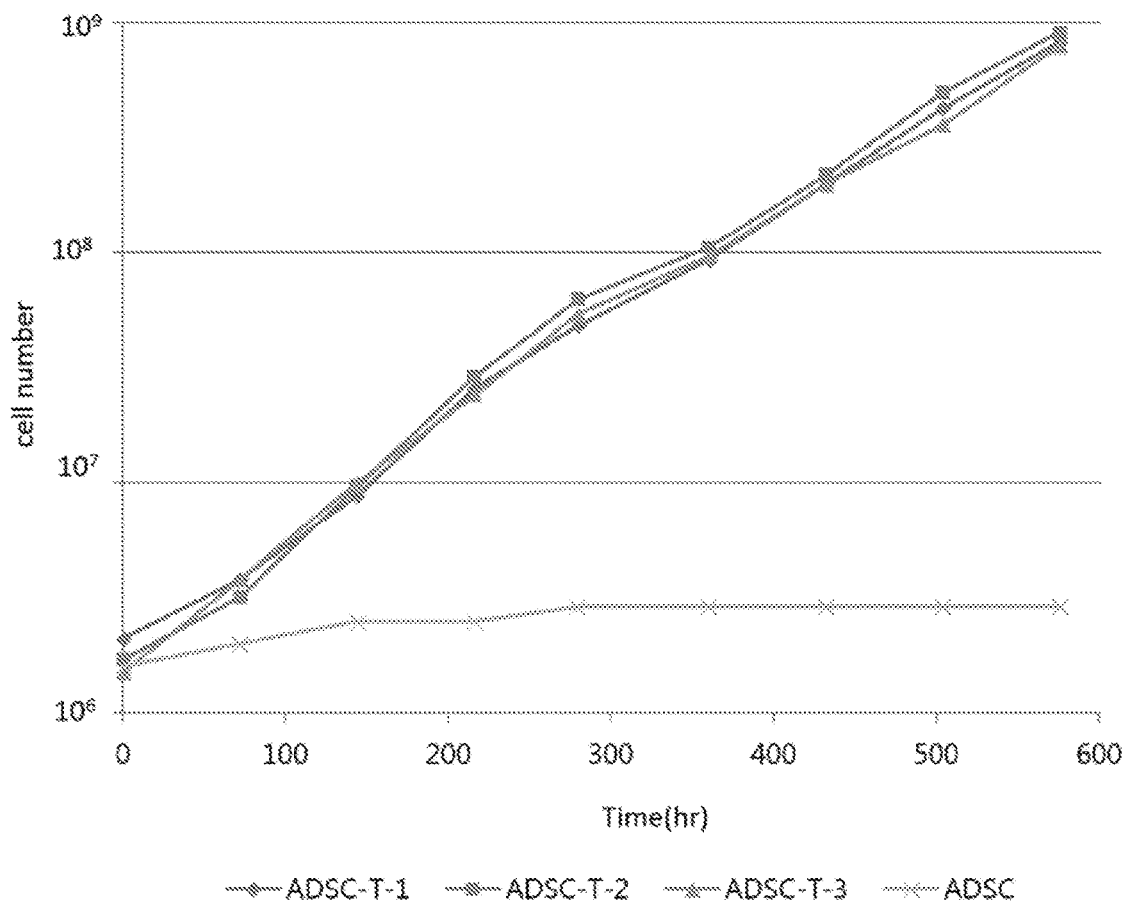
FIG. 6 is a diagram illustrating the proliferation rates of the primary ADSC and three cells (ADSC-T-1, ADSC-T-2, and ADSC-T-3) of ADSC-T.

The results are illustrated in FIG. 6.

As illustrated in FIG. 6, it was confirmed that while the primary adipose-derived stem cells (primary ADSC) were subjected to cell division once at intervals of about 6 to days, the three ADSC-T cells were subjected to cell division once at intervals of about 2 days. In addition, in the case of the primary adipose-derived stem cells (primary ADSC), the proliferation rate was gradually decreased, and thus, the extinction phenomenon was exhibited. However, in the case of the ADSC-T, even though the three cell lines were slightly different, the lifespan of the cells was generally extended, and the proliferation rate was fast. The improvement of the proliferation rate was continuously maintained for about 6 months (50 sub-cultivation times), and after that, the proliferation rate of the cell was decreased.

<Example 5> Verification of Hair Growth Effect of ADSC-T Cell Culture Medium

In order to confirm a hair growth effect of the culture medium of the ADSC-T cells, the animal experiment was carried out by using female C57BL/6 mice. In detail, using 6 weeks C57BL/6 mice, the hairs of abdominal regions were primarily removed by using a clipper for an animal, and then, secondly, the remained hairs were completely removed by using a general depilatory for 2 to 3 minutes. Then, the hairs were completely removed and clearly cleaned. As an experiment group, the culture medium of ADSC-T was used and as a control group, normal saline solution was used. Total 12 mice used for the experiment were used, and 6 mice were assigned for each of the groups. At daily 11 a.m. from next day after removing the hairs, the skin application of the experimental solutions was carried out by applying once like massage using a sterilized cotton swab after dropping 150 μl every time on the abdominal region without hairs for 3 weeks.

The ADSC-T cells were cultured in 1×105 cell/ml, respectively, and when the cell confluence reached 80%, after 2 days, the culture solution was collected. The collected culture solution was centrifuged at 800 G for 3 minutes to remove the cellular residue and obtain only a supernatant. The obtained culture supernatant was used for the experiments.

In order to confirm a hair growth state, the mice were lightly subjected to insufflations narcosis using ether at intervals of 6 days after the experiment initiation, and then, the abdominal regions of the mice were observed with the naked eyes.

The results obtained by observing the abdominal regions of the mice, without hairs, with the naked eyes are illustrated in FIG. 7, and the days required to exhibit the blue spots are illustrated in FIG. 8.

As illustrated in FIG. 7, it was confirmed that in the case of the experiment groups applied with the culture medium of an adipose-derived stem cells (ADSC-T), the blue spots were exhibited on the pink abdominal region of one mouse after 4 days of the application, and the skin color was changed. After 5 days of the application, it was confirmed that the skin colors on 3 mice were changed. The skin color on one mouse was changed at 6 days and also the skin color on one mouse was changed at 7 days. As a result, it was confirmed that after one week, all the 6 mice of the experiment group exhibit blue spots on their abdominal regions, and their skin colors were changed. Meanwhile, it was confirmed that in the case of the control group applied with normal saline solution, after 4 days, the skin color of one mouse was changed, after 8 days, the skin color of another one mouse was changed, after 10 days, the skin color of one mouse was changed, after 13 days, the skin colors of two mice were changed, after 15 days, the skin color of one mouse was changed, and after two weeks, the abdominal colors of all the mice in the control group were changed.

In addition, as illustrated in FIG. 8, it was confirmed that the blue spots exhibited on the abdominal regions of the mice of the experiment group, which were applied with the culture medium of ADSC-T, were changed into the black color at the time, As illustrated in FIG. 8, it was confirmed that the blue spots exhibited in the abdominal regions of the mice in the experimental group, which are applied with the culture medium of ADSC-T, were changed in a black color as time passes, and thus, the hairs were grown. After 12 days, the colors of the abdominal regions of three mice that were half was changed into a black color, and thus, the hairs were started to be grown. For three remained mice, the blue spot area became wider, and the concentration of blue color grown rich in color. After about 3 weeks, it was confirmed that for the hairless areas in all of 6 mice, hairs were grown, and thus, there was a hair growth effect.

Meanwhile, in the case of the control group, the abdominal regions of all the mice after 2 weeks exhibited the blue spots, but except in the case of one mouse that firstly exhibits the blue spots, the colors of the abdominal regions of the mice were not changed into a black color even during 3 weeks, and the hairs were not grown. However, in the case of the mouse that firstly exhibited the blue spots, the color of the abdominal region was changed into a black color at 15 days, and the hairs were grown.

From the above results, it was confirmed that for all the mice applied with the culture medium of ADSC-T cells, the skin colors in the abdominal regions without hairs were changed from a pink color to a black color, and thus, the hairs were grown. Therefore, it can be confirmed that the culture medium of ADSC-T cell has a hair grown effect.

INDUSTRIAL APPLICABILITY

The adipose-derived stem cell (ADSC-T) according to the present invention exhibits long lifespan, improved cell proliferation rate, and extended proliferation period, as compared with a primary adipose-derived stem cell (ADSC), and thus, the adipose-derived stem cell (ADSC-T) can be usefully used for the study about the adipose-derived stem cell and the mass production of the culture medium of the adipose-derived stem cell. In addition, according to the present invention, the culture medium of the adipose-derived stem cell (ADSC-T) that expresses a T antigen of SV40 exhibits excellent hair growth effectiveness and can be usefully used as a raw material for the hair loss prevention and hair growing agents.

The invention claimed is:

1. A method for promoting hair growth by administering to a subject in need thereof an effective amount of a pharmaceutical composition comprising a culture medium of an adipose-derived stem cell expressing a T antigen of SV40 (ADSC-T) as an active component.

2. A method for promoting hair growth by administering to a subject in need thereof an effective amount of a cosmetic composition comprising a culture medium of an adipose-derived stem cell expressing a T antigen of SV40 (ADSC-T) as an active component.

* * * * *